US00PP08218P

United States Patent [19]

Christensen

[11] Patent Number: Plant 8,218

[45] Date of Patent: May 4, 1993

[54] ROSE PLANT JACMAGI

[75] Inventor: Jack E. Christensen, Ontario, Calif.

[73] Assignee: Bear Creek Gardens, Inc., Medford, Oreg.

[21] Appl. No.: 775,300

[22] Filed: Oct. 10, 1991

[51] Int. Cl.[5] ..... A01H 5/00
[52] U.S. Cl. ..... Plt./24
[58] Field of Search ..... Plt./24, 15

*Primary Examiner*—James R. Feyrer
*Assistant Examiner*—E. F. McElwain
*Attorney, Agent, or Firm*—Klarquist, Sparkman, Campbell, Leigh & Whinston

[57] ABSTRACT

A new rose variety is disclosed having very deep-yellow buds that are resistant to color change as the bud opens. Open-flower color is also deep yellow. The flowers are borne either singly or in clusters of up to about 3-7 blooms. The plant has an upright growth habit and dark green, leathery, glossy foliage. The new variety was created by crossing the variety Meigronuri (U.S. Plant Pat. No. 4,625) with the variety Tansenfrie.

1 Drawing Sheet

The present invention relates to a new and distinct variety of rose plant of the Floribunda class which was originated by me by crossing the variety Meigronuri, U.S. Plant Pat. No. 4,625, with the variety Tansenfrie.

The primary objective of this breeding was to produce a new rose variety having the deep-yellow flowers and disease resistance of Meigronuri combined with the taller, more upright habit and smaller bloom-cluster size of Tansenfrie. This objective was substantially achieved along with other desirable improvements as evidenced by the following unique combination of characteristics which are outstanding in the new variety and which distinguish it from its parents, as well as from all other varieties of which I am aware:

1. Very deep-yellow bud and open flower that is resistant to color change;
2. Flowers borne singly and in clusters of three to seven;
3. Upright habit of growth; and
4. Dark green, leathery, glossy foliage.

Asexual reproduction of this new variety by budding, as performed at Wasco, Calif., shows that the foregoing characteristics and distinctions come true to form and are established and transmitted through succeeding propagations.

The accompanying color photograph shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Meigronuri, U.S. Plant Pat. No. 4,625.

*Pollen parent.*—Tansenfrie.

Classification:

*Botanical.*—*Rosa hybrida.*

*Commercial.*—Floribunda.

FLOWER

Observations made from specimens grown in a garden environment in Somis, Calif., in April-June, 1991.

Blooming habit: Recurrent.

Bud:

*Size.*—1½ inches when the petals start to unfurl.

*Form.*—Pointed ovoid.

*Color.*—When sepals first divide, bud color is Yellow Group 9A. When half blown, the upper sides of the petals are Yellow Group 9B; and the lower sides of the petals are Yellow Group 9B.

*Sepals.*—Color: Green Group 138C. Surface texture: Covered with fine hairs. There are three lightly appendaged sepals. There are two unappendaged sepals with hairy edges.

*Receptacle.*—Color: Green Group 143A. Shape: Apple. Size: Large, broad, ½ inch by ½ inch. Surface: Smooth with a few fine hairs.

*Peduncle.*—Length: Short (1½ inches to 1¾ inches). Surface: Smooth, but has numerous smooth hairs. Color: Medium green. Strength: Stiff, erect.

Bloom:

*Size.*—Large. Average open diameter is 4 inches.

*Borne.*—Singly, several together, and in flat clusters.

*Stems.*—Medium, 12 inches to 14 inches.

*Form.*—When first open: High centered. Permanence: Bloom flattens as it ages. Outer petals curl back, with some quilling.

*Petalage.*—Number of petals under normal conditions: 20.

*Color.*—The upper sides of the petals are Yellow Group 9A. The reverse sides of the petals are Yellow Group 9A. The bases of the petals are Yellow Group 9A. The major color on the upper sides of the petals is Yellow Group 9A.

*Variegations.*—None.

*Discoloration.*—No change in the general tonality at the end of the first day. By the end of the third day, there is a light and very gradual fading to Yellow Group 9B.

*Fragrance.*—Moderate.

Petals:

*Texture.*—Thick and leathery.
*Shape.*—Round.
*Form.*—Tips slightly recurved, edges slightly quilled.
*Arrangement.*—Imbricated, with no petaloids in the center.
*Persistence.*—Drop off cleanly.
*Lastingness.*—On the plant: Fair, 4 to 5 days. As a cut flower: Fair, 5 days.

Reproductive parts:
*Anthers.*—Size: Medium. Quantity: Many. Color: Yellow. Arrangement: Regular around styles.
*Filaments.*—Color: Gold yellow.
*Pollen.*—Color: Gold yellow.
*Styles.*—Color: Greenish white.
*Stigmas.*—Color: Greenish white.

Form: Bush.

Growth: Vigorous, upright, branching.

Foliage:
*Number of leaflets on normal mid-stem leaves.*—5 or 7.
*Size.*—Large, 5 inches long by 3½ inches wide.
*Quantity.*—Abundant.
*Color.*—New foliage: Reddish. Old foliage: Dark green, glossy.

Leaflets:
*Shape.*—Pointed oval.
*Texture.*—Upper side: Leathery and glossy.
*Edge.*—Serrated.

*Serration.*—Single and small.
*Petiole rachis.*—Color: Green.
*Petiole underside.*—Rough, with prickles.
*Stipules.*—Long (1 inch), bearded.
*Disease resistance.*—Resistant to mildew under normal growing conditions at Somis, Calif.

Wood:
*New wood.*—Color: Light green. Bark: Smooth.
*Old wood.*—Color: Green. Bark: Smooth.

Prickles:
*Quantity.*—Ordinary number on main canes from base and on laterals from main canes.
*Form.*—Medium, straight to hooked slightly downward.
*Color when young.*—Red.

Small prickles:
*Quantity.*—On main stalks: None. On laterals: None.

I claim:

1. A new and distinct variety of rose plant of the Floribunda class, substantially as herein shown and described, characterized particularly as to novelty by the unique combination of its very deep yellow formed buds and the buds' resistance to fading as the flower opens, by its upright habit of growth, its well-formed flower clusters and single flowers, and its dark green leathery foliage.

* * * * *

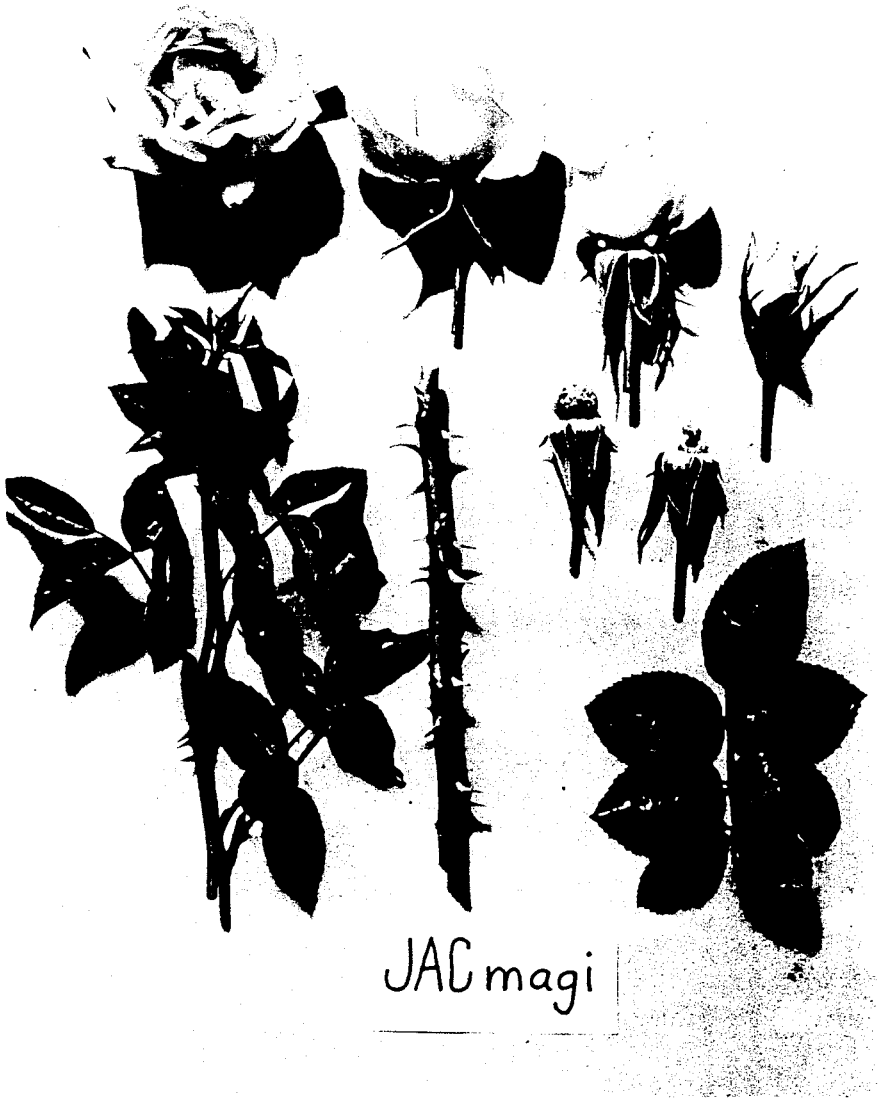
JAC magi